(12) United States Patent
Ouchi

(10) Patent No.: US 7,749,156 B2
(45) Date of Patent: Jul. 6, 2010

(54) RETRACTABLE TREATMENT INSTRUMENT FOR ENDOSCOPE

(75) Inventor: Teruo Ouchi, Saitama (JP)

(73) Assignee: Hoya Corporation, Tokyo (JP)

( * ) Notice: Subject to any disclaimer, the term of this patent is extended or adjusted under 35 U.S.C. 154(b) by 686 days.

(21) Appl. No.: 11/086,305

(22) Filed: Mar. 23, 2005

(65) Prior Publication Data

US 2005/0215853 A1  Sep. 29, 2005

(30) Foreign Application Priority Data

Mar. 24, 2004  (JP)  ............... 2004-085846
Mar. 31, 2004  (JP)  ............... 2004-101659

(51) Int. Cl.
*A61B 1/00* (2006.01)

(52) U.S. Cl. ............ 600/104; 600/106; 606/46

(58) Field of Classification Search ........ 600/106, 600/107, 127, 131, 139, 104; 606/1, 41–52, 606/31
See application file for complete search history.

(56) References Cited

U.S. PATENT DOCUMENTS

| | | | |
|---|---|---|---|
| 4,492,832 A | | 1/1985 | Taylor |
| 4,733,662 A | | 3/1988 | DeSatnick et al. |
| 5,053,041 A | * | 10/1991 | Ansari et al. ............ 606/1 |
| 5,401,274 A | | 3/1995 | Kusunoki |
| 5,423,814 A | * | 6/1995 | Zhu et al. ............ 606/46 |
| 5,460,629 A | | 10/1995 | Shlain et al. |
| 5,542,945 A | | 8/1996 | Fritzsch |
| 5,899,850 A | | 5/1999 | Ouchi |
| 6,007,514 A | | 12/1999 | Nita |
| 6,193,717 B1 | | 2/2001 | Ouchi |
| 6,299,625 B1 | * | 10/2001 | Bacher ............ 606/170 |
| 6,409,727 B1 | * | 6/2002 | Bales et al. ............ 606/41 |
| 6,428,503 B1 | | 8/2002 | Kierce |
| 6,605,104 B2 | * | 8/2003 | Sato et al. ............ 606/206 |
| 6,767,348 B2 | | 7/2004 | Nakada et al. |
| 6,949,099 B2 | * | 9/2005 | Shiro et al. ............ 606/45 |

(Continued)

FOREIGN PATENT DOCUMENTS

DE  3707820  9/1987

(Continued)

OTHER PUBLICATIONS

English Language Abstract of JP 8-299355.

(Continued)

*Primary Examiner*—Michael Peffley
*Assistant Examiner*—Victoria W Chen
(74) *Attorney, Agent, or Firm*—Greenblum & Bernstein P.L.C.

(57) ABSTRACT

A retractable treatment instrument for an endoscope is provided. The retractable treatment instrument includes a flexible sheath configured such that at least a tip portion thereof is formed of a flexible tube, an operation wire inserted in the flexible sheath so as to be movable along an axial direction of the operation wire in the flexible sheath, and a front-end treatment member attached to a tip of the operation wire. In this structure, the front-end treatment member is movable back and forth along the axial direction with respect to a tip of the flexible sheath. The front-end treatment member has a wide part elongated in a radial direction of the flexible tube to press and broaden the flexible tube from an inside of the flexible tube.

12 Claims, 23 Drawing Sheets

U.S. PATENT DOCUMENTS

| | | |
|---|---|---|
| 2002/0120253 A1 | 8/2002 | Ouchi |
| 2003/0040744 A1 | 2/2003 | Latterell et al. |
| 2003/0144663 A1* | 7/2003 | Berberich et al. ............ 606/46 |
| 2003/0225312 A1 | 12/2003 | Suzuki et al. |
| 2004/0039249 A1 | 2/2004 | Shiro et al. |
| 2005/0177151 A1* | 8/2005 | Coen et al. ................... 606/41 |

FOREIGN PATENT DOCUMENTS

| | | |
|---|---|---|
| EP | 0919196 | 6/1999 |
| EP | 1234543 | 8/2002 |
| JP | 1-201248 | 8/1989 |
| JP | 7-008503 | 1/1995 |
| JP | 8-299355 | 11/1996 |
| JP | 2002-113015 | 4/2002 |
| JP | 2002-153484 | 5/2002 |
| JP | 2002-253559 | 9/2002 |
| JP | 2003-299663 | 10/2003 |
| WO | 01/58360 | 8/2001 |

OTHER PUBLICATIONS

English Language Abstract of JP 7-008503.
English Language Abstract of JP 1-201248.
English Language Abstract of JP 2002-253559.
English Language Abstract of JP 2002-153484.
U.S. Appl. No. 11/086,436, filed Mar. 23, 2005.

* cited by examiner

RETRACTABLE TREATMENT INSTRUMENT FOR ENDOSCOPE

BACKGROUND OF THE INVENTION

The present invention relates to a retractable treatment instrument to be inserted into an instrument-inserting channel of an endoscope.

There are a large number of types of treatment instruments for endoscopes. For example, Japanese Patent Provisional Publication Number HEI 8-299355 discloses one of such treatment instruments for endoscopes. The treatment instrument disclosed in the publication includes a front-end treatment member connected to a leading end of an operation wire inserted into a flexible sheath to be movable along an axial direction of the flexible sheath. The treatment instrument is used, for example, as a high-frequency incision instrument.

SUMMARY OF THE INVENTION

However, a conventional treatment instrument disclosed in the publication has a drawback that the protruding length of the front-end treatment member from a tip of the flexible sheath can not be kept constant at states other than a state where the front-end treatment member is protruded at the maximum from the tip of the flexible sheath and a state where the front-end treatment member is fully retracted into a tip portion of the flexible sheath.

The conventional treatment instrument has another drawback that the front-end treatment member may be forced to rotate at the tip portion of the flexible sheath about an axis thereof if the front-end treatment member is pressed against a mucous membrane.

Therefore, there may be a case where an operator can not perform an endoscopic treatment as intended.

The present invention is advantageous in that it provides a retractable treatment instrument configured such that the protruding length from a tip of a flexible sheath can be adjusted at desired lengths so that an endoscopic treatment can be performed as desired by an operator.

According to an aspect of the invention, there is provided a retractable treatment instrument for an endoscope, which is provided with a flexible sheath configured such that at least a tip portion thereof is formed of a flexible tube, an operation wire inserted in the flexible sheath so as to be movable along an axial direction of the operation wire in the flexible sheath, and a front-end treatment member attached to a tip of the operation wire. In this structure, the front-end treatment member is movable back and forth along the axial direction with respect to a tip of the flexible sheath. The front-end treatment member has a wide part elongated in a radial direction of the flexible tube to press and broaden the flexible tube from an inside of the flexible tube.

With this configuration, it is possible to securely hold the front-end treatment member at a desirable position while setting the protruding length of the front-end treatment member from the tip of the flexible sheath at a desired length.

Optionally, the wide part may be formed in a vicinity of a base portion of the front-end treatment member.

Still optionally, the retractable treatment instrument may include an operation unit attached to a base of the flexible sheath. The operation unit may have a movable hook connected to a base of the operation wire to move back and forth the operation wire in the axial direction.

Still optionally, the operation wire may be rotatable about an axis line thereof relative to the flexible sheath.

Still optionally, the retractable treatment instrument may include a holding ring attached to a base portion of the flexible sheath so that the operation wire is rotated about the axis line while holding the holding ring.

Still optionally, an extension of the tip of the operation wire may coincide with a center axis of the wide part.

In a particular case, at least a tip portion of the front-end treatment member may be formed to be a flat rod-like shape.

In a particular case, the front-end treatment member may be formed to have a pad-like part at a tip thereof.

In a particular case, the front-end treatment member may be formed to be a flat rod-like shape, and a pad-like part may be formed at a tip portion of the front-end treatment member by elongating the flat rod-like shape at the tip portion of the front-end treatment member.

Optionally, the flexible sheath may have at least one expanded part in which the wide part of the front-end treatment member fits, and the at least one expanded part is located at a part of the flexible sheath formed of the flexible tube.

Still optionally, when the wide part the front-end treatment member is situated in the at least one expanded part of the flexible sheath, the front-end treatment member may be fully retracted into the flexible sheath.

Still optionally, the at least one expanded part may include a plurality of expanded parts, and the plurality of expanded parts may be arranged along an axial direction of the flexible sheath.

Still optionally, when the wide part of the front-end treatment member fits in a rear end expanded part of the plurality of expanded parts nearest to a base of the flexible sheath, the front-end treatment member may be fully retracted into the flexible sheath. When the wide part of the front-end treatment member fits in one of the plurality of expanded parts other than the rear end expanded part, the front-end treatment member may protrude from the tip of the flexible sheath by a predetermined length.

In a particular case, the expanded part may be formed by expanding the flexible tube uniformly in a radial direction of the flexible tube.

In a particular case, the at least one expanded part may be formed by pressing a part of the flexible tube from both sides of the flexible tube so that the part of the flexible tube is expanded in a direction perpendicular to a pressing direction in which the flexible tube is pressed.

In a particular case, the flexible tube may have a cut off part which is formed by cutting off a part of the at least one expanded part projected outward from an outside diameter the flexible tube.

In a particular case, the retractable treatment instrument may satisfy a condition:

$$1.07d \leq W \leq 1.26d$$

where W represents a width of the wide part in an elongated direction, and d represents an internal diameter of the flexible sheath.

In a particular case, corners of the wide part may be cut away such that an edge of the wide part bends at predetermined degrees at each corner portion of the wide part.

BRIEF DESCRIPTION OF THE ACCOMPANYING DRAWINGS

DETAILED DESCRIPTION OF THE EMBODIMENTS

Hereinafter, embodiments according to the invention are described with reference to the accompanying drawings.

First Embodiment

Figure 2:
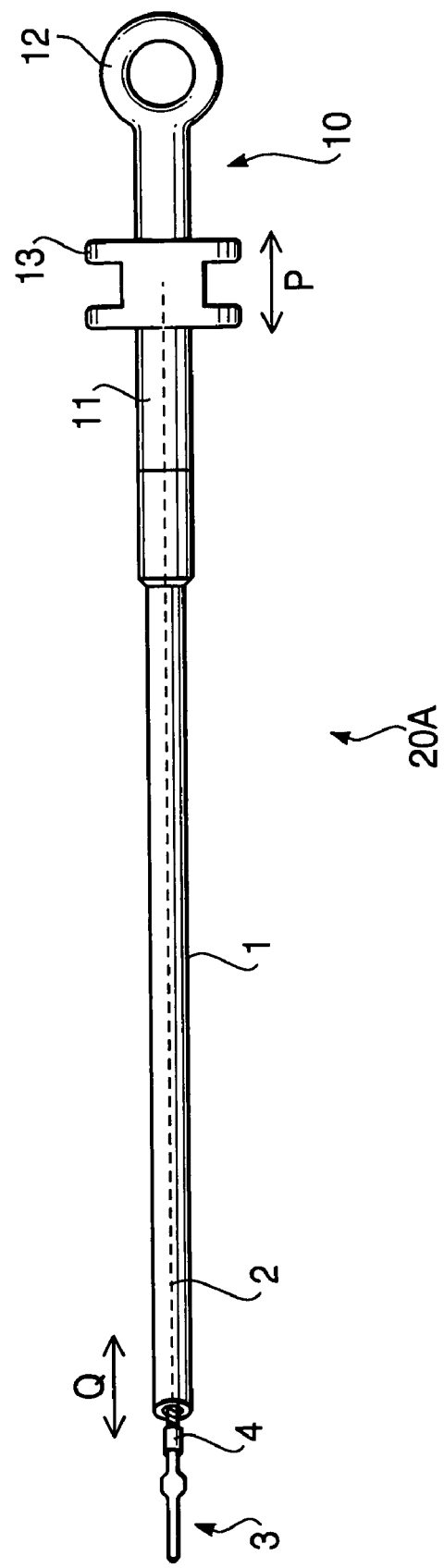
FIG. 2 is a general view of the retractable treatment instrument according to the first embodiment.

FIG. 2 is a general view of a retractable treatment instrument 20A for endoscopes according to a first embodiment of the invention. The retractable treatment instrument 20A includes a flexible sheath 1 formed of an insulative flexible tube such as a tetrafluoroethylene resin tube. A conductive operation wire 2 is disposed in the inside of the flexible sheath 1 along the length of the flexible sheath 1 so that the operation wire 2 is movable along an axial direction of the operation wire 2. The flexible sheath 1 may be configured such that at least a tip portion thereof is formed of a flexible tube.

A front-end treatment member 3 (for example, formed of a stainless steel plate) is connected to a tip of the operation wire 2 via a connection pipe 4 (for example, formed of a stainless steel pipe) so that the front-end treatment member 3 is retractable with respect to the tip of the flexible sheath 1. That is, the front-end treatment member 3 moves forward or backward with respect to the tip of the flexible sheath 1.

At a base part of the flexible sheath 1, an operation unit 10 is connected. The operation unit 10 is used to move the operation wire 2 along the axial direction of the operation wire 2 in the flexible sheath 1. The operation unit 10 includes an operation main body 11, a fixed hook 12 formed at a base end of the operation main body 11, and a movable hook 13 slidably attached to the operation main body 11. A base of the operation wire 2, which is pulled straight in the flexible sheath 1 toward the operation unit 10, is connected to the movable hook 13.

In this structure, the operation wire 2 moves along the axial direction in the flexible sheath 1 by operating the movable hook 13 to move in a direction P. As a result, the front-end treatment member 3 is protruded from or retracted into the tip portion of the flexible sheath 1 as indicated by a double-headed arrow Q shown in FIG. 2.

Figure 1:
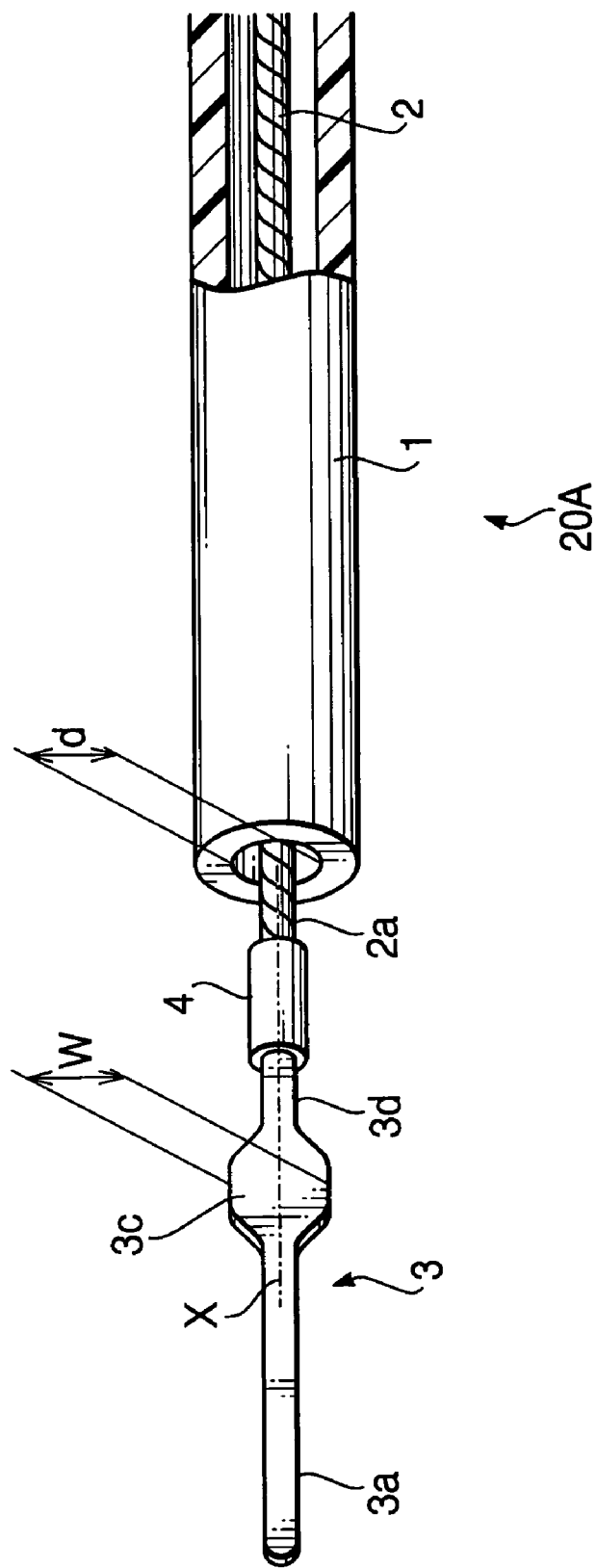
FIG. 1 is an enlarged view of a tip portion of a retractable treatment instrument according to a first embodiment.

FIG. 1 is an enlarged view of the tip portion of the retractable treatment instrument 20A. As shown in FIG. 1, the front-end treatment member 3 has a rod-like part 3a having a slender flat shape along an axial direction of the flexible sheath 1. The rod-like part 3a functions as a needle-like surgical knife. The retractable treatment instrument 20A may be formed such that a high-frequency current can be passed through the front-end treatment member 3 via the operation wire 2.

At the base portion of the front-end treatment member 3, a wide part 3c is formed. The wide part 3c may be formed by elongating a part of the base portion of the front-end treatment member 3 in both directions opposed to each other with respect to a central axis of the front-end treatment member 3. The central axis X of the wide part 3c coincides with an extension of a central axis of a tip portion 2a of the operation wire 2.

As shown in FIG. 1, corners of the wide part 3c are cut away such that an edge of the wide part 3c bends at 45 degrees at each corner portion. Alternatively, each corner part may be cut away so that the edge has a round shape at each corner portion. A slender part 3d is formed at the base of the wide part 3c so as to be connected to the connection pipe 4.

The wide part 3c is configured to have a width W larger than an internal diameter d of the flexible sheath 1 to some extent (i.e. W>d). For example, if the internal diameter d is 1.5 mm, a difference (W−d) may be within 0.1 through 0.4 mm (i.e. $1.07d \leq W \leq 1.26d$).

Figure 3:
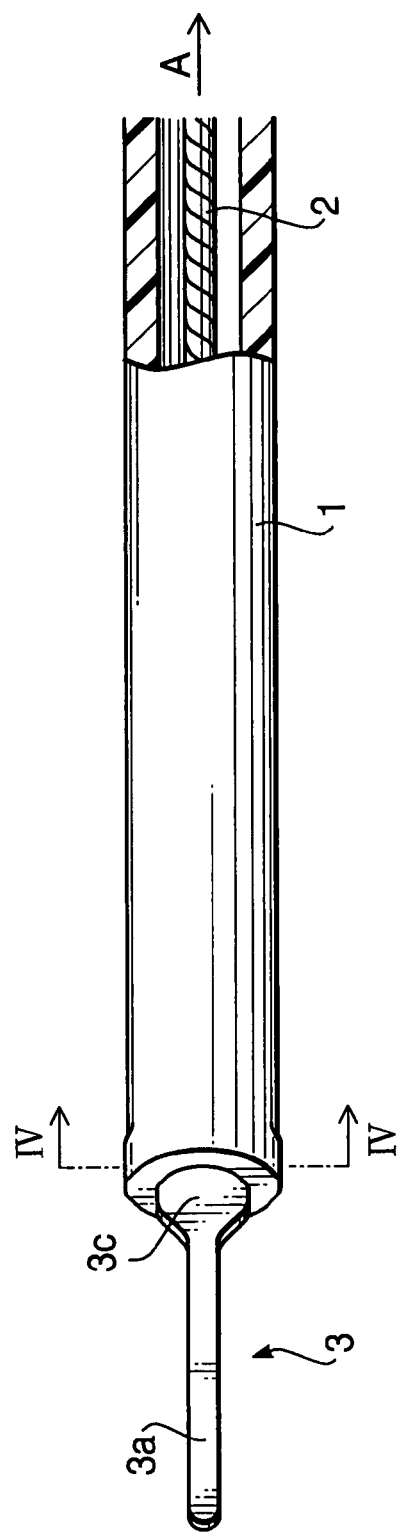
FIG. 3 is a side perspective view of the retractable treatment instrument illustrating a situation where a wide part of a front-end treatment member is retracted into a tip portion of a flexible sheath.
Figure 4:
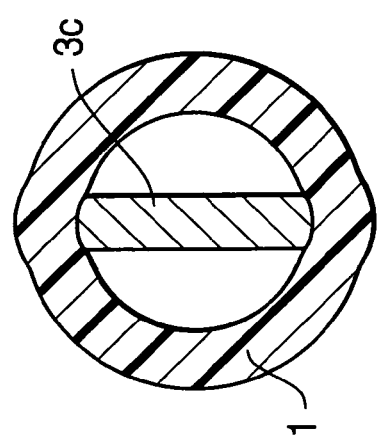
FIG. 4 is a cross-sectional view of the retractable treatment instrument along a line IV-IV of FIG. 3.

Therefore, if the operation wire 2 is pulled in a direction A shown in FIG. 3 by operating the operation unit 10 to retract the wide part 3c into the inside of the tip portion of the flexible sheath 1, the wide part 3c fits into the inside of the tip portion (i.e. a flexible tube part) of the flexible sheath 1 in such a manner that the edge of the wide part 3c presses and broadens the inner surface of the flexible sheath 1 as illustrated in FIG. 4 which is a cross-sectional view of the retractable treatment instrument 20A along a line IV-IV of FIG. 3. In this state, the front-end treatment member 3 is securely held by the inner surface of the flexible sheath 1.

Figure 5:
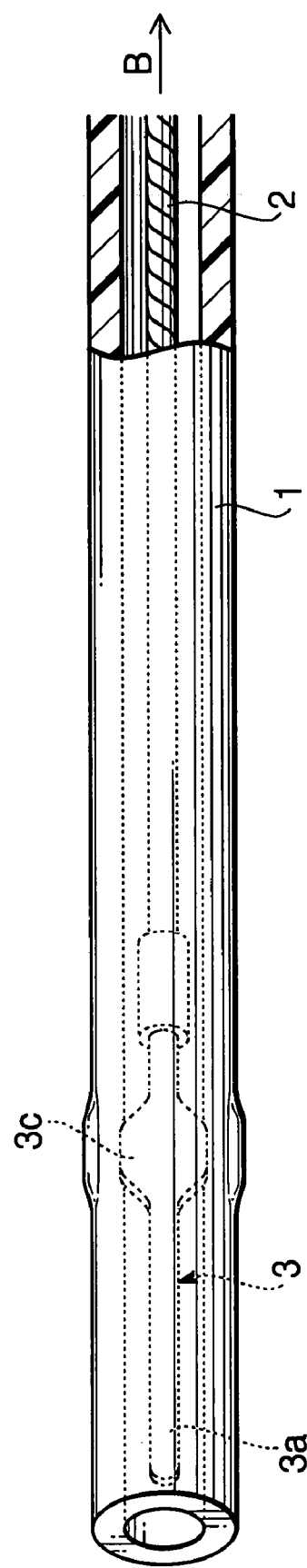
FIG. 5 is a side perspective view of the retractable treatment instrument illustrating a situation where the front-end treatment member is fully retracted into the tip portion of the flexible sheath.

If the operation wire 2 is pulled at the maximum in a direction B shown in FIG. 5 by operating the operation unit 10, the front-end treatment member 3 is fully retracted into the tip portion of the flexible sheath 1 as illustrated in FIG. 5.

Figure 6:
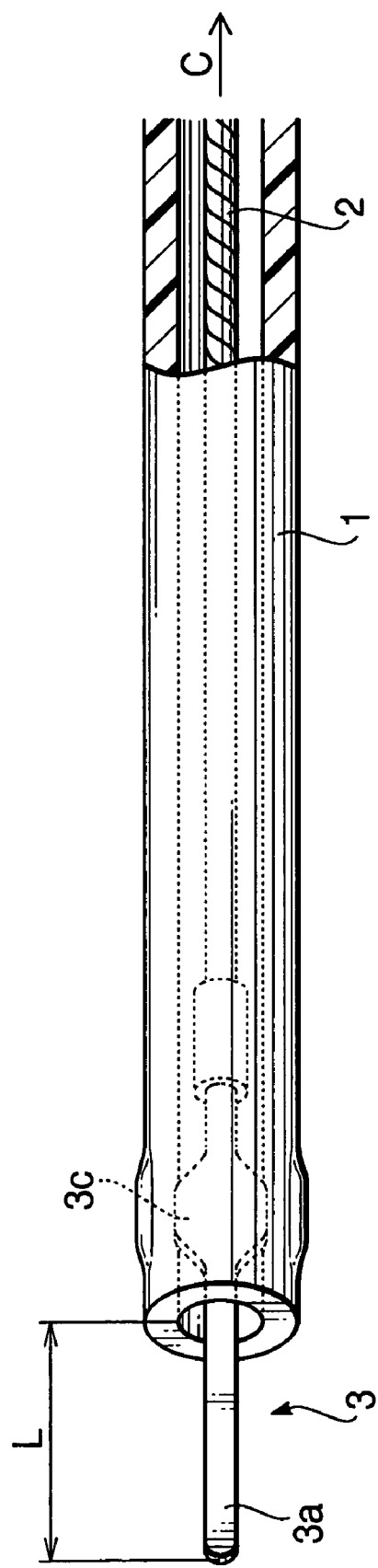
FIG. 6 is a side perspective view of the retractable treatment instrument illustrating a situation where a half of the front-end treatment member is retracted into the tip portion of the flexible sheath.

By operating the movable hook 13 to move the operation wire 2 in a direction C shown in FIG. 6, the front-end treatment member 3 can be fixed at desired positions. For example, the front-end treatment member 3 can be fixed at a position at which the front-end treatment member 3 is protruded by a desirable length L from the tip of the flexible sheath 1.

In this state, the front-end treatment member 3 is fixed in the tip portion of the flexible sheath 1 by a reaction force applied to the edge of the wide part 3c by the flexible sheath 1. Therefore, even if an external force smaller than a fixing force of the flexible sheath 1 acts on the front-end treatment member 3, the front-end treatment member 3 does not move with respect to the tip of the flexible sheath 1.

Therefore, occurrence of an undesirable phenomenon that the front-end treatment member 3 moves backward into the tip portion of the flexible sheath 1 when the front-end treatment member 3 is pressed by an operator against a mucous membrane is prevented. It becomes possible to perform an endoscopic treatment as desired by an operator.

Second Embodiment

Figure 7:
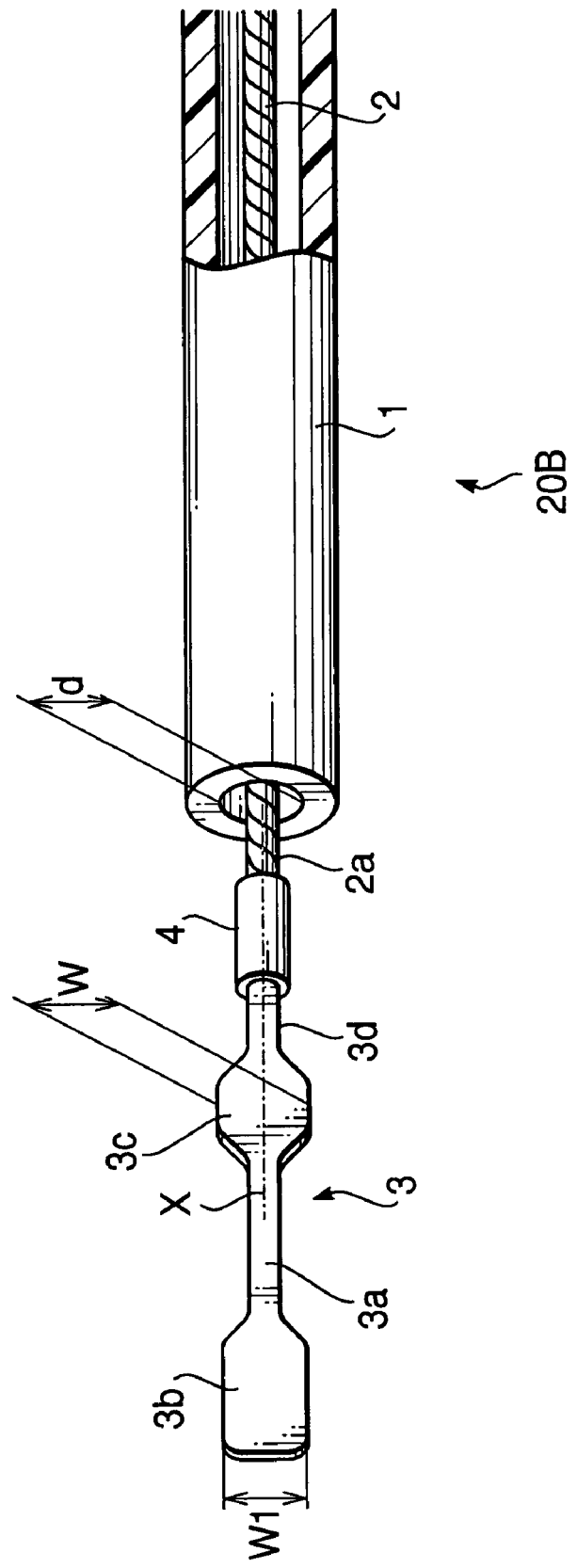
FIG. 7 is an enlarged view of a tip portion of a retractable treatment instrument for endoscopes according to a second embodiment of the invention.
Figure 8:
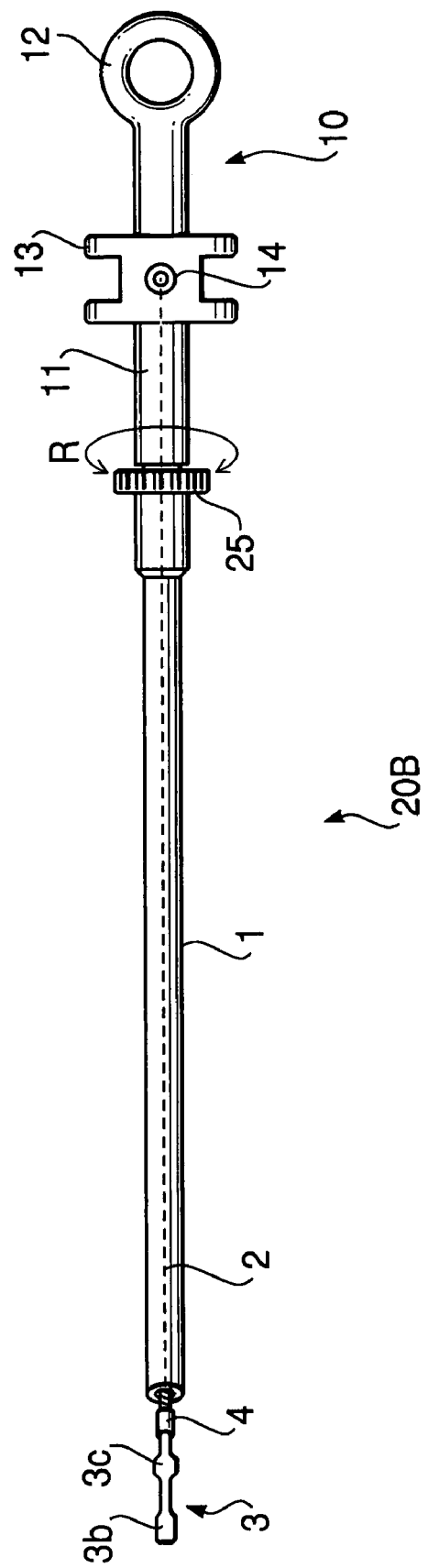
FIG. 8 is a general view of the retractable treatment instrument according to the second embodiment.

FIG. 7 is an enlarged view of a tip portion of a retractable treatment instrument 20B for endoscopes according to a second embodiment of the invention. FIG. 8 is a general view of the retractable treatment instrument 20B according to the second embodiment. In FIGS. 7 and 8 (and in the other drawings of the second embodiment), to elements which are similar to those of the first embodiment, the same reference numbers are assigned, and the detailed description thereof will not be repeated.

One of the features of the retractable treatment instrument 20B according to the second embodiment is that a paddle 3b is formed at a tip of the rod-like part 3a of the front-end treatment member 3. The paddle 3b is configured to have a width W1 which is substantially equal to the width W of the wide part 3c or smaller than the width W to some extent.

As shown in FIG. 8, a connector 14 to which a high-frequency power source cable can be connected is located on the movable hook 13 of the operation unit 10, so that a high-frequency current can be supplied to the front-end treatment member 3 via the operation wire 2.

The base part of the flexible sheath 1 is attached to the operation main body 11 such that the flexible sheath 1 is fixed in the axial direction thereof and is rotatable about the axis thereof. At the base of the flexible sheath 1, a holding ring 25 is fixed.

By operating the operation unit 10 to rotate about the axis as illustrated by an arrow R in FIG. 8 while holding the holding ring 25, the operation wire 2 rotates about the axis in the flexible sheath 1 and the front-end treatment member 3 rotates about the axis. Therefore, the operator can set the direction of the paddle 3b of the front-end treatment member 3 at a desirable direction by operating the operation unit 10 in a state in which the front-end treatment member 3 fully protrudes from the tip of the flexible sheath 1.

Figure 9:
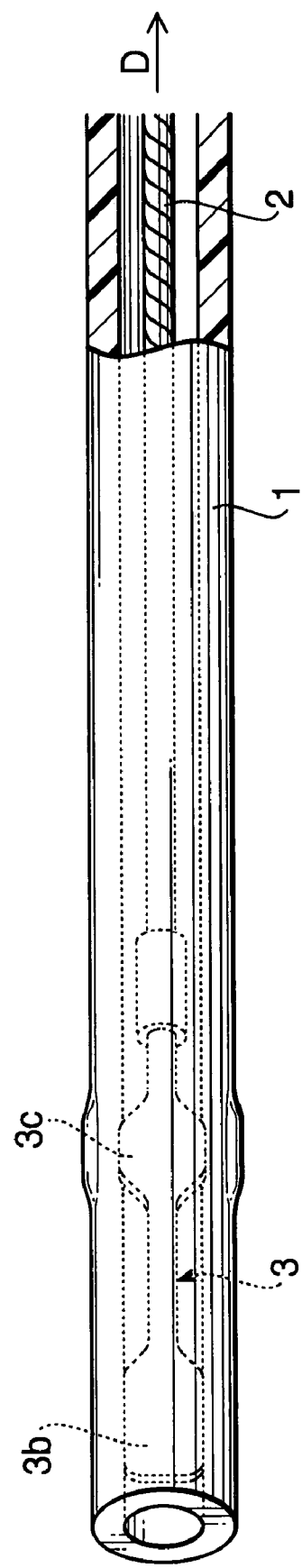
FIG. 9 is a side perspective view of the retractable treatment instrument according to the second embodiment, illustrating a situation where a front-end treatment member is fully retracted into the tip portion of a flexible sheath.

If the operation wire 2 is pulled at the maximum in a direction D shown in FIG. 9 by operating the operation unit 10, the front-end treatment member 3 is fully retracted into the tip portion of the flexible sheath 1 as illustrated in FIG. 9.

Figure 10:
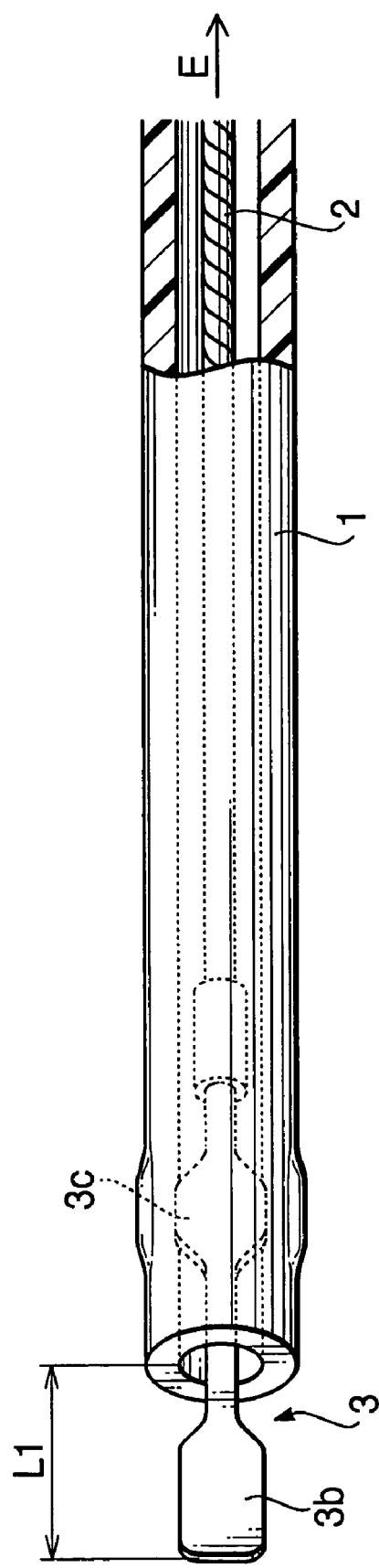
FIG. 10 is a side perspective view of the retractable treatment instrument according to the second embodiment, illustrating a situation where the front-end treatment member is retracted to the midpoint of the tip portion of the flexible sheath.

By operating the movable hook 13 to move the operation wire 2 in a direction E shown in FIG. 10, the front-end treatment member 3 can be fixed at desired positions. For example, the front-end treatment member 3 can be fixed at a position at which the front-end treatment member 3 is protruded by a desirable length L1 from the tip of the flexible sheath 1.

In this state, the front-end treatment member 3 is fixed in the tip portion of the flexible sheath 1 by a reaction force applied to the edge of the wide part 3c by the flexible sheath 1. Therefore, even if an external force smaller than a fixing force of the flexible sheath 1 acts on the paddle 3b, the front-end treatment member 3 does not move in the axial direction and does not rotate about the axis with respect to the tip of the flexible sheath 1.

Figure 11:
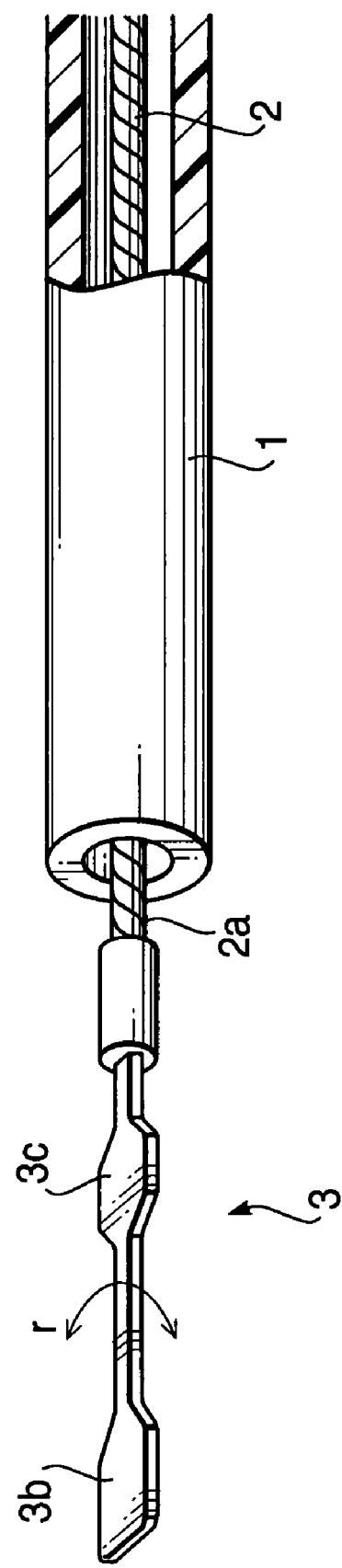
FIG. 11 is a side perspective view of the tip portion of the retractable treatment instrument according to the second embodiment, illustrating a situation where the front-end treatment member is rotated about a center axis of the front-end treatment member.

If the front-end treatment member 3 fully protrudes from the tip of the flexible sheath 1, the direction (i.e. a rotational position about the axis of the front-end treatment member 3) of the paddle 3 can be set at a desirable direction by operating the operation unit 10 as indicated by an arrow r in FIG. 11.

Figure 12:
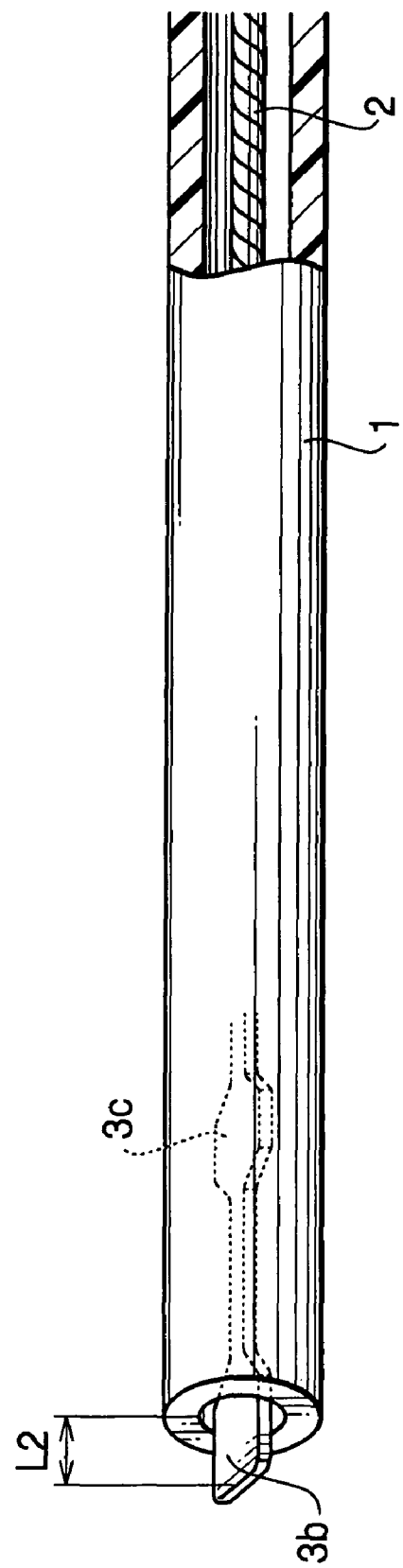
FIG. 12 is a side perspective view of the tip portion of the retractable treatment instrument according to the second embodiment, illustrating a situation where a half of a paddle is retracted into the tip portion of the flexible sheath after the front-end treatment member is rotated.

By retracting the front-end treatment member 3 into the tip portion of the flexible sheath 1 by operating the operation unit 10 after the direction of the paddle 3b is adjusted at a desired direction, the paddle 3 is fixed at the desired direction while the protruding length from the tip of the flexible sheath 1 is set at a desired length L2 (see FIG. 12). Therefore, a high-frequency incision treatment can be performed in a safe condition using the retractable treatment instrument 20B.

Figure 13:
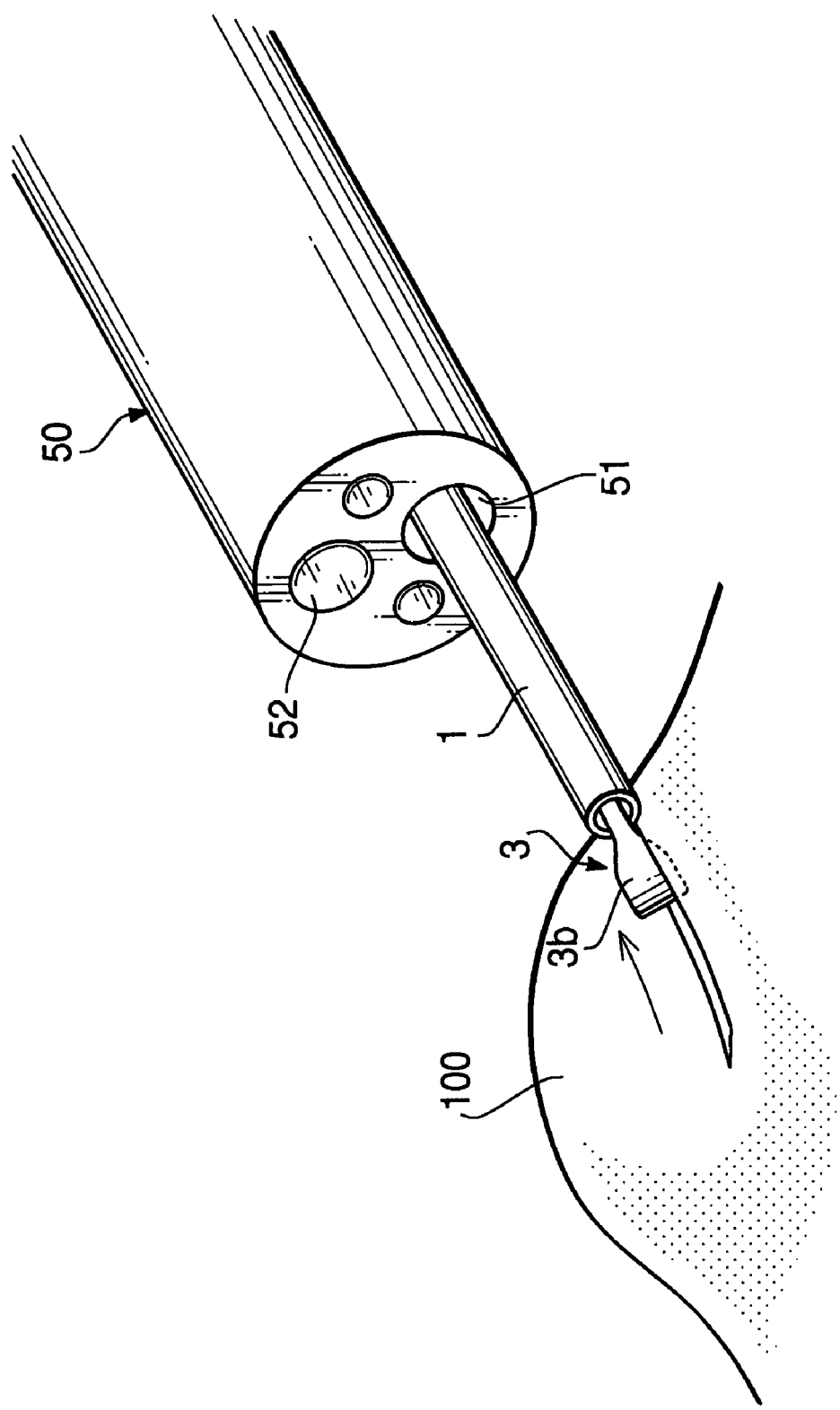
FIG. 13 shows a situation where a mucous membrane is cut by using the retractable treatment instrument according to the second embodiment.
Figure 14:
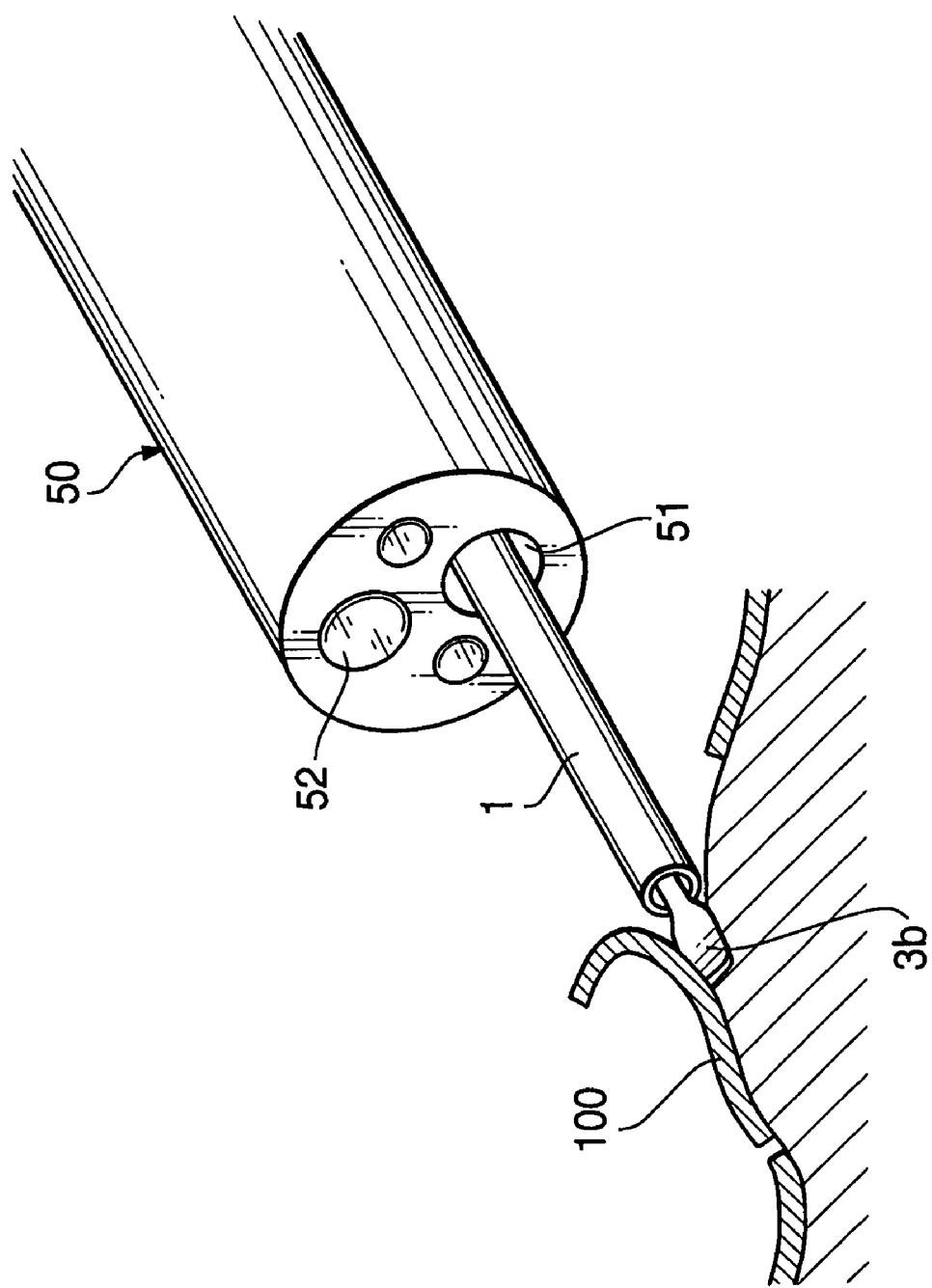
FIG. 14 shows a situation where a part of a mucous membrane is ablated by using the retractable treatment instrument according to the second embodiment.

FIG. 13 shows a situation where a mucous membrane 100 is cut by using the retractable treatment instrument 20B which is inserted into an instrument-inserting channel 51 of an endoscope 50. Such an endoscopic operation is performed by observing the mucous membrane 100 through an observation window 52. In FIG. 13, an operator operates the retractable treatment instrument 20B so that the paddle 3b is perpendicularly pressed against the mucous membrane 100. FIG. 14 shows a situation where a part of the mucous membrane 100 is ablated by using the retractable treatment instrument 20B which is inserted into the instrument-inserting channel 51 of the endoscope 50. In FIG. 14, the paddle 3b is positioned horizontally with respect to an inner surface of the mucous membrane 100 and is inserted under the inner surface of the mucous membrane 100 to perform an ablation treatment of mucous membrane 100.

Figure 15:
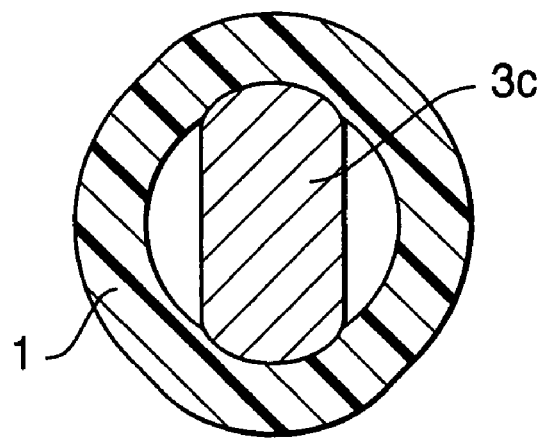
FIGS. 15 and 16 show other examples of a cross-sectional shape of the wide part.
Figure 16:
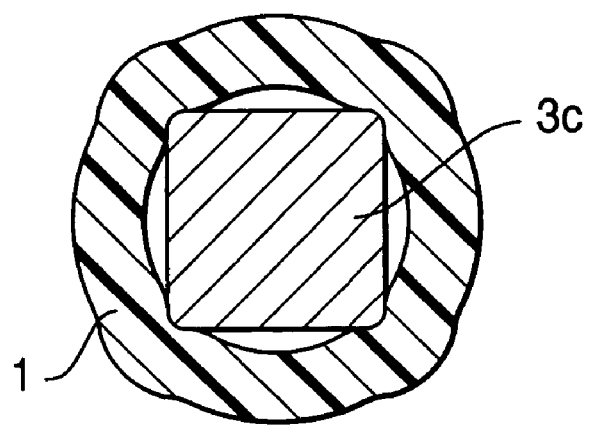

FIGS. 15 and 16 show other examples of a cross-sectional shape of the wide part 3c. In the example of FIG. 15, the wide part 3c has an elliptical cross-sectional form (along a line IV-IV of FIG. 3). In the example of FIG. 16, the wide part 3c has a rectangular cross-sectional form (along a line IV-IV of FIG. 3).

Third Embodiment

Figure 17:
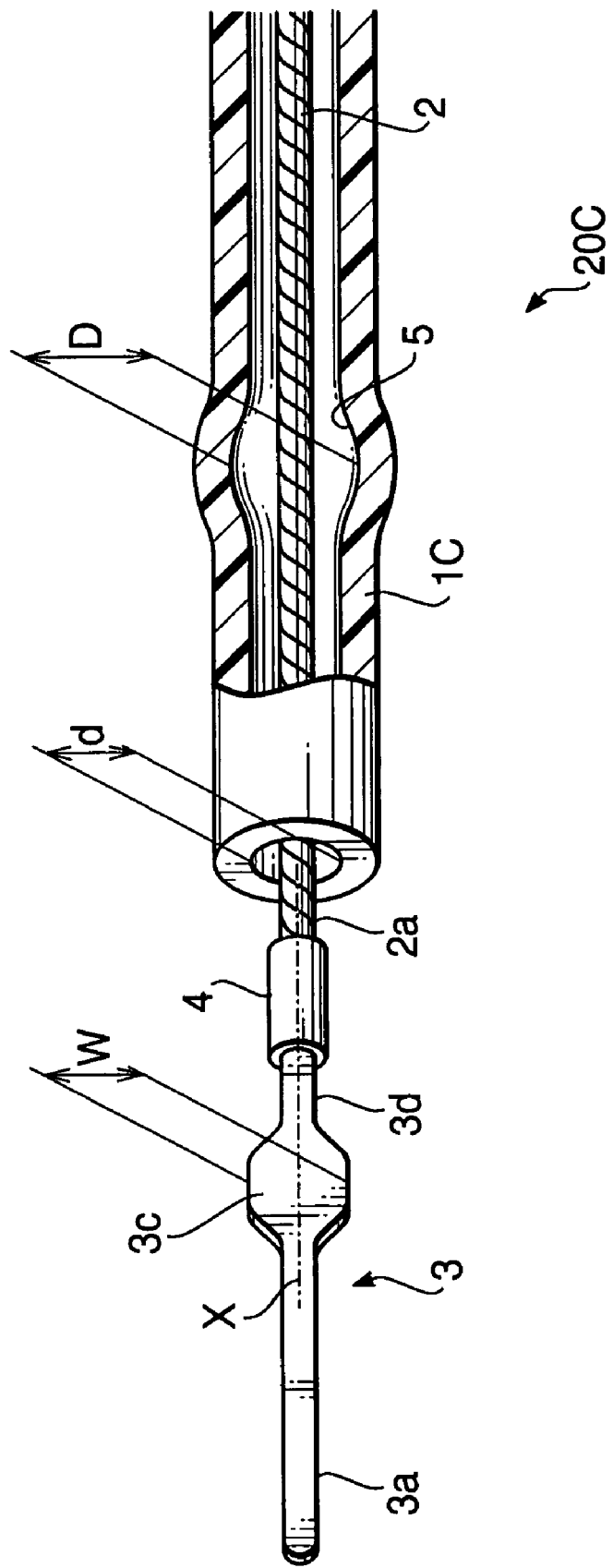
FIG. 17 is an enlarged view of a tip portion of a retractable treatment instrument according to a third embodiment.
Figure 18:
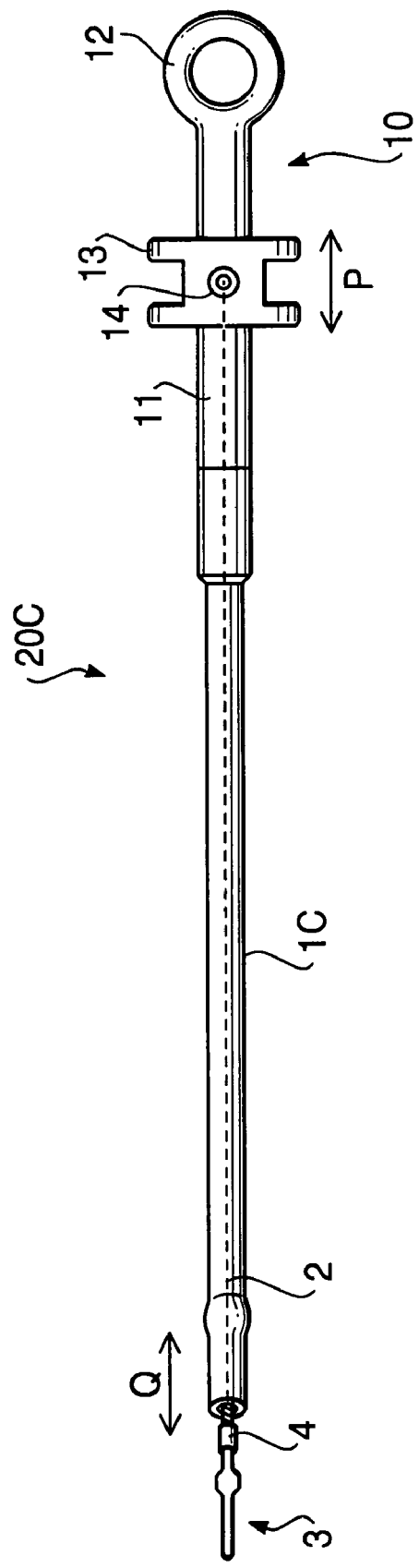
FIG. 18 is a general view of the retractable treatment instrument according to the third embodiment.

FIG. 17 is an enlarged view of a tip portion of a retractable treatment instrument 20C for endoscopes according to a third embodiment of the invention. FIG. 18 is a general view of the retractable treatment instrument 20C according to the third embodiment. In FIGS. 17 and 18 (and in the other drawings of the third embodiment), to elements which are similar to those of the first and second embodiments, the same reference numbers are assigned, and the detailed description thereof will not be repeated.

Similarly to the second embodiment, the retractable treatment instrument 20C is provided with the connector 14 to which a high-frequency power source cable is connected. Therefore, the retractable treatment instrument 20C is used as a high-frequency incision instrument. If the retractable treatment instrument 20C is used as a mechanical incision instrument, it is not necessary to connect the high-frequency power source cable to the connector 14.

Figure 19:
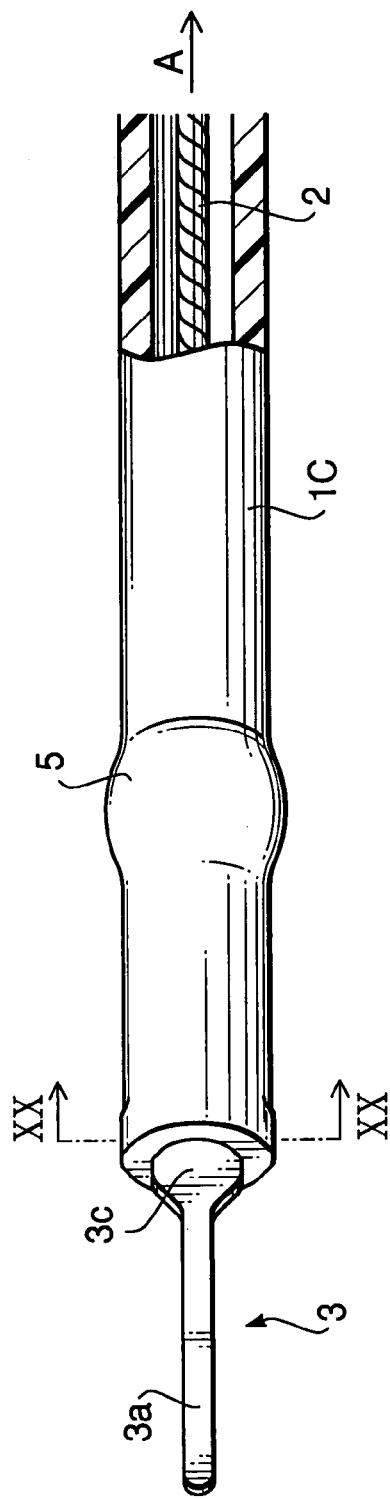
FIG. 19 is a side perspective view of the retractable treatment instrument according to the third embodiment, illustrating a situation where a wide part of a front-end treatment member is retracted into a tip portion of a flexible sheath.
Figure 20:
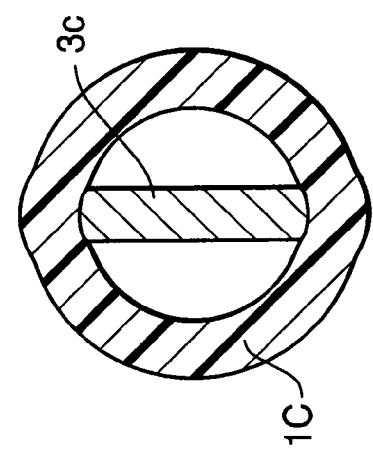
FIG. 20 is a cross-sectional view of the retractable treatment instrument according to the third embodiment along a line XX-XX of FIG. 19.

If the operation wire 2 is pulled in a direction A shown in FIG. 19 by operating the operation unit 10 to retract the wide part 3a into the inside of the tip portion of a flexible sheath 1C, the wide part 3c fits into the inside of the tip portion (i.e. a flexible tube part) of the flexible sheath 1 in such a manner that the edge of the wide part 3c presses and broaden the inner surface of the flexible sheath 1C as illustrated in FIG. 20 which is a cross-sectional view the retractable treatment instrument 20A along a line XX-XX of FIG. 19. In this state, the front-end treatment member 3 is securely held by the inner surface of the flexible sheath 1C.

As shown in FIG. 17, an expanded part 5 is formed in the vicinity of the tip of the flexible sheath 1C. The expanded part 5 has an adequate size to hold the wide part 3c of the front-end treatment member 3. The expanded part 5 is formed by expanding a part of the flexible sheath 1C uniformly in a radial direction. The inner diameter D of the expanded part 5 is equal to or slightly larger than the width W of the wide part 3c (i.e. D≧W).

Figure 21:
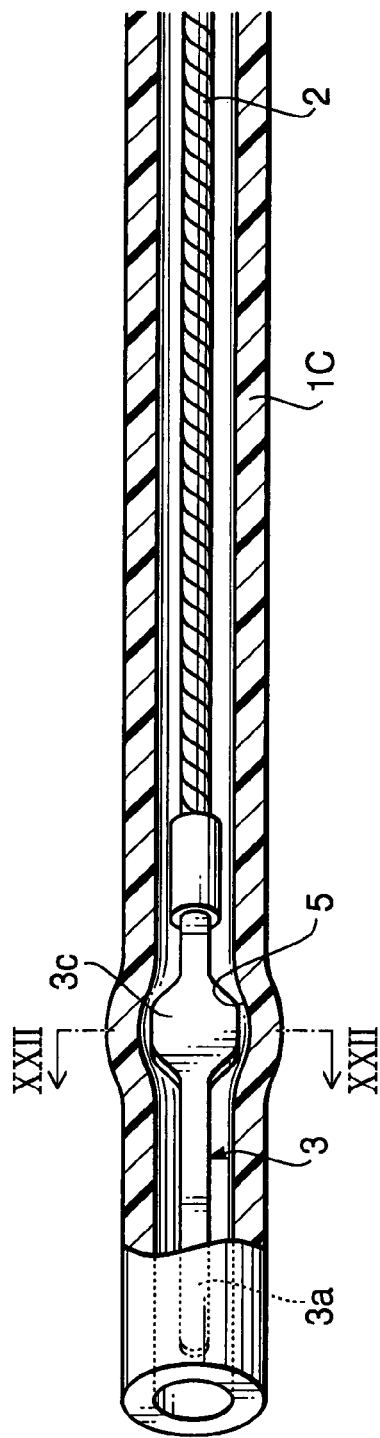
FIG. 21 is a side perspective view of the retractable treatment instrument according to the third embodiment, illustrating a situation where the front-end treatment member is fully retracted into the tip portion of the flexible sheath.

As shown in FIG. 21, in a state where the wide part 3c engages with the expanded part 5 of the flexible sheath 1C, the front-end treatment member 3 is fully retracted into the tip portion of the flexible sheath 1C.

Therefore, by further pulling the operation wire 2 from the state of FIG. 19, the wide part 3c moves backward while the wide part 3c presses the inner surface of the tip portion of the flexible sheath 1C and produces the friction between the edge of the wide part 3c and the inner surface of the flexible sheath 1C. If the wide part 3c reaches the position of the expanded part 5, the friction between the edge of the wide part 3c and the inner surface of the sheath 1C becomes substantially zero. In this state, the wide part 3c fits into the expanded part 5 as illustrated in FIG. 22 which is a cross-sectional view the retractable treatment instrument 20C along a line XXII-XXII of FIG. 21.

Figure 22:
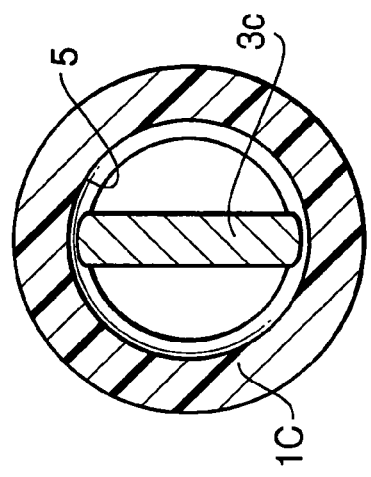
FIG. 22 is a cross-sectional view along a line XXII-XXII of FIG. 21.

In the state of FIG. 22, the wide part 3c does not get out of the expanded part 5 unless the operation wire 2 is pulled or pressed by a force larger than a certain strength (which is adequate to press and expand the inner surface of the flexible sheath 1C). Therefore, by locating the wide part 3c of the front-end treatment member 3 at the position of the expanded part 5 before attachment work where the retractable treatment instrument 20C is inserted into an instrument-inserting channel of an endoscope, it becomes possible to prevent the front-end treatment member 3 from getting out of the tip of the flexible sheath 1C and thereby damaging an inner wall of the instrument-inserting channel of the endoscope during the attachment work.

Figure 23:
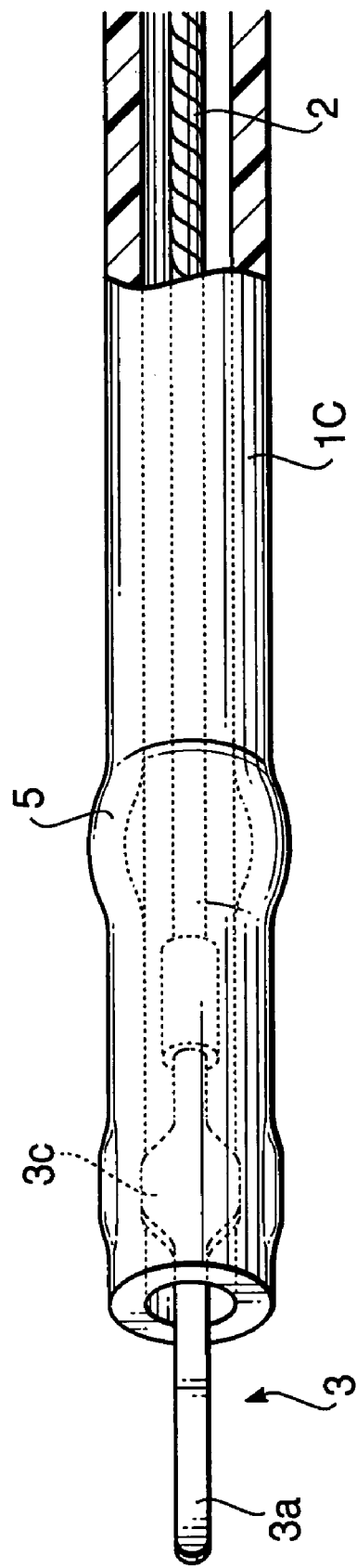
FIG. 23 is a side perspective view of the retractable treatment instrument according to the third embodiment, illustrating a situation where a half of the front-end treatment member is retracted into the tip portion of the flexible sheath.

By pressing the operation wire 2 by a force larger than the certain strength by operating the operation unit 10 to move forward the front-end treatment member 3 to a position shown in FIG. 23, the front-end treatment member 3 is securely held at the position shown in FIG. 23. That is, an endoscopic treatment can be performed in a safe condition while the protruding length of the rod-like part 3a from the tip of the flexible sheath 1C is set at a desired length.

Fourth Embodiment

Figure 24:
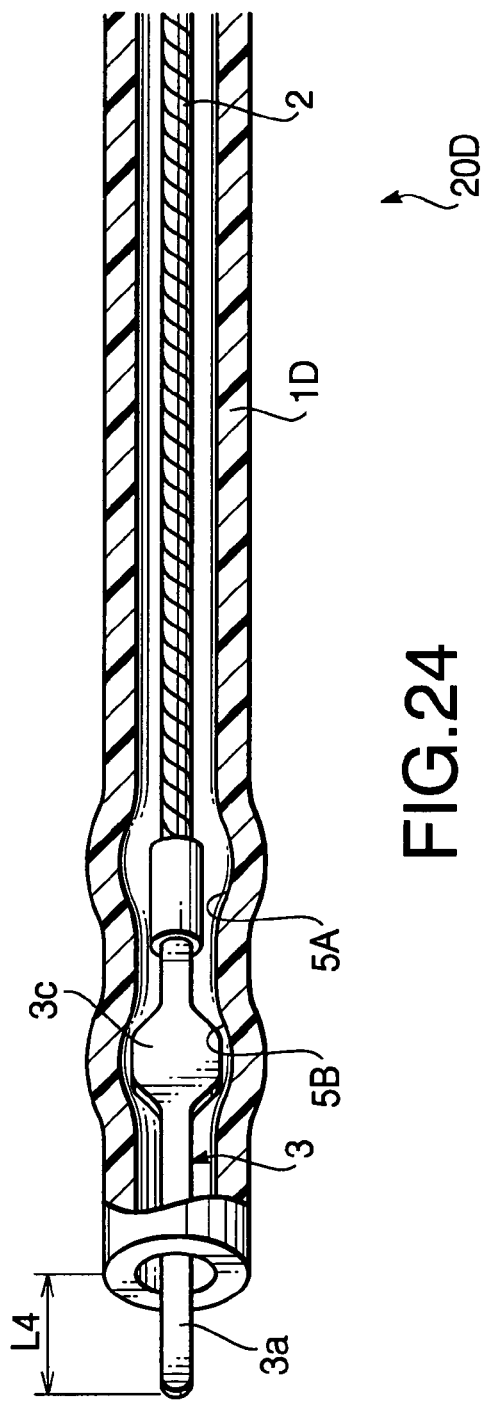
FIG. 24 is a side perspective view of a tip portion of a retractable treatment instrument according to a fourth embodiment.

FIG. 24 is an enlarged view of a tip portion of a retractable treatment instrument 20D for endoscopes according to a fourth embodiment of the invention. In FIG. 24 (and in the other drawings of the fourth embodiment), to elements which are similar to those of the first through third embodiments, the same reference numbers are assigned, and the detailed description thereof will not be repeated.

As shown in FIG. 24, a flexible sheath 1D has rear and front expanded parts 5A and 5B at positions along the lengthwise direction of the flexible sheath 1D. When the wide part 3c of the front-end treatment member 3 is located at a position of the rear expanded part 5A, the front-end treatment member 3 is fully retracted into the tip portion of the flexible sheath 1D. When the wide part 3c of the front-end treatment member 3 is located at a position of the front expanded part 5B, the front-end treatment member 3 is held at a position at which the protruding length of the rod-like part 3a from the tip of the flexible sheath 1D is set at a length L4.

Although the flexible sheath 1D is configured to have two expanded parts in this embodiment, the flexible sheath may be condfigured to have three or more expanded parts to securely fix the front-end treatment member 3 at desirable positions.

Since the wide part 3c is securely held in the expanded part 5B, the state where the protruding length of the rod-like part 3a from the tip of the flexible sheath 1C is L4 is securely maintained. The protruding length of L4 does not change unless an external force larger than a certain strength (which is adequate to press and expand the inner surface of the flexible sheath 1D) acts on the front-end treatment member 3. Accordingly, an endoscopic treatment can be performed in a safe condition while the protruding length of the rod-like part 3a from the tip of the flexible sheath 1C is set at a desired length.

Fifth Embodiment

Figure 25:
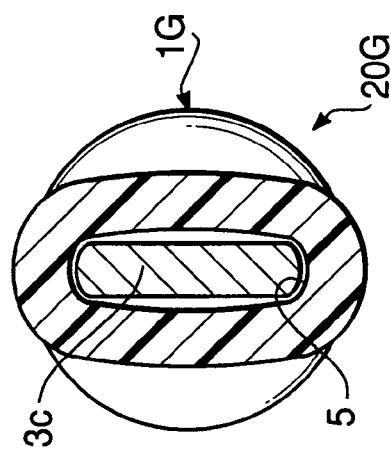
FIG. 25 is a cross-sectional view of a retractable treatment instrument according to a fifth embodiment.

FIG. 25 shows a cross-sectional shape of a flexible sheath 1G of a retractable treatment instrument 20G according to a fifth embodiment of the invention. The cross-sectional shape of FIG. 25 corresponds to the cross-sectional shape along a line XXII-XXII of FIG. 21. The expanded part 5 shown in FIG. 25 is formed by pressing a part of the flexible sheath 1G from both sides of the flexible sheath 1G (for example, while heating the part of the flexible sheath 1G) so that the part of the flexible sheath 1G is expanded in a direction perpendicular to a pressing direction in which the flexible sheath 1G is pressed.

Sixth Embodiment

Figure 26:
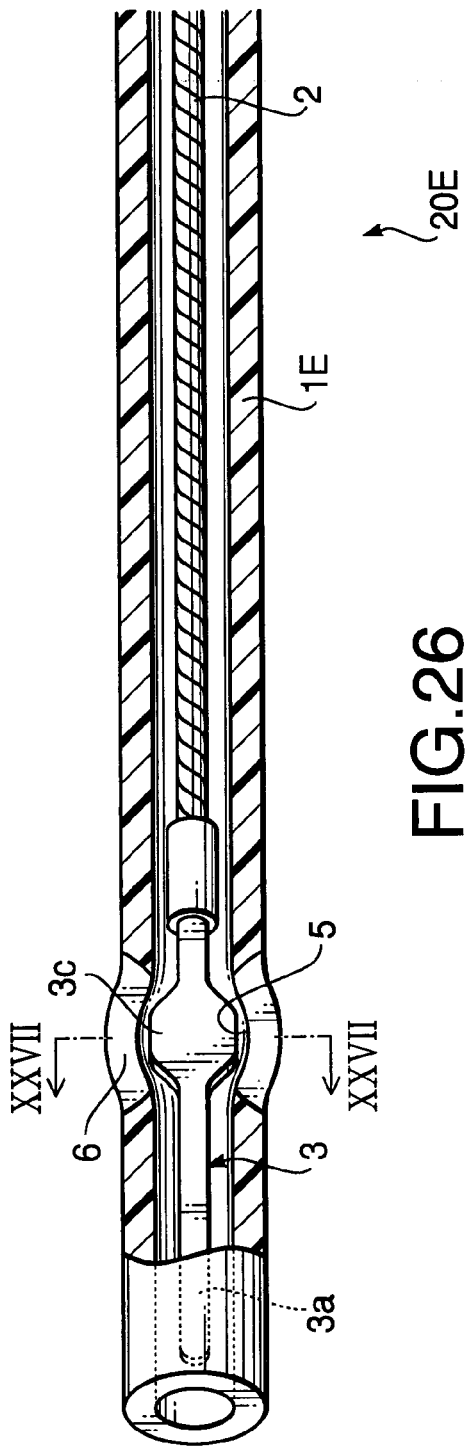
FIG. 26 is a side cross-sectional view of a tip portion of a retractable treatment instrument according to a sixth embodiment.
Figure 27:
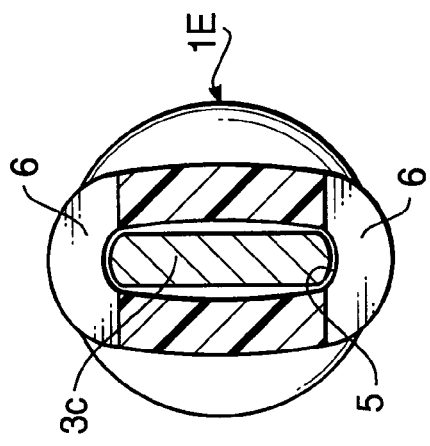
FIG. 27 is a cross sectional view of a flexible sheath according to the sixth embodiment along a line XXVII-XXVII of FIG. 26.

FIG. 26 is a side cross-sectional view of a tip portion of a retractable treatment instrument 20E for endoscopes according to a sixth embodiment of the invention. FIG. 27 is a cross sectional view of a flexible sheath 1E according to the sixth embodiment along a line XXVII-XXVII of FIG. 26. In FIGS. 26 and 27, to elements which are similar to those of the first through fifth embodiments, the same reference numbers are assigned, and the detailed description thereof will not be repeated.

The flexible sheath 1E has cut off parts 6 which is formed, for example, by cutting off a part of the expanded part 5 (which may be formed by a process described in the fifth embodiment) projected outward from the outside diameter of the flexible sheath 1E.

With this structure, degradation of workability of inserting the retractable treatment instrument 20E into an instrument-inserting channel of an endoscope due to an expanded part formed on the flexible sheath is prevented. Since the cut off part 6 is formed, the wide part 3c engages with the expanded part 5 more securely. That is, the wide part 3c is held at a position of the cut off part 6 securely.

Seventh Embodiment

Figure 28:
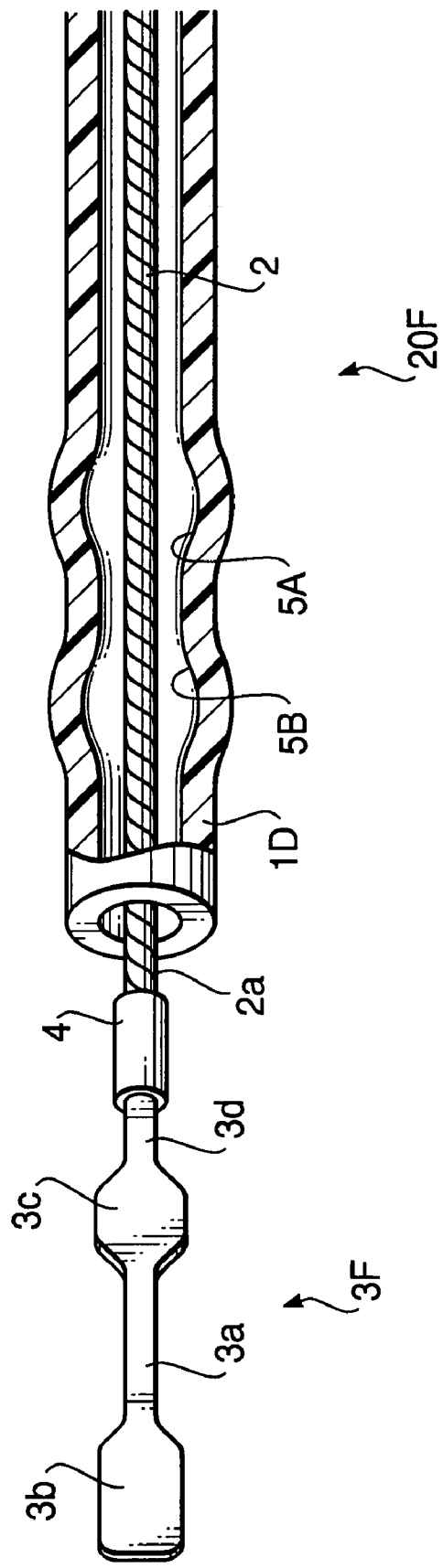
FIG. 28 is a perspective view of a tip portion of a retractable treatment instrument according to a seventh embodiment.

FIG. 28 is a perspective view of a tip portion of a retractable treatment instrument 20F for endoscopes according to a seventh embodiment of the invention. In FIG. 28, to elements which are similar to those of the first through sixth embodiments, the same reference numbers are assigned, and the detailed description thereof will not be repeated.

Similarly to the fourth embodiment, the retractable treatment instrument 20F includes the flexible sheath 1D having two expanded parts 5A and 5B. As shown in FIG. 28, the paddle 3b is formed at the tip pf the rod-like part 3a of the front-end treatment member 3.

Figure 29:
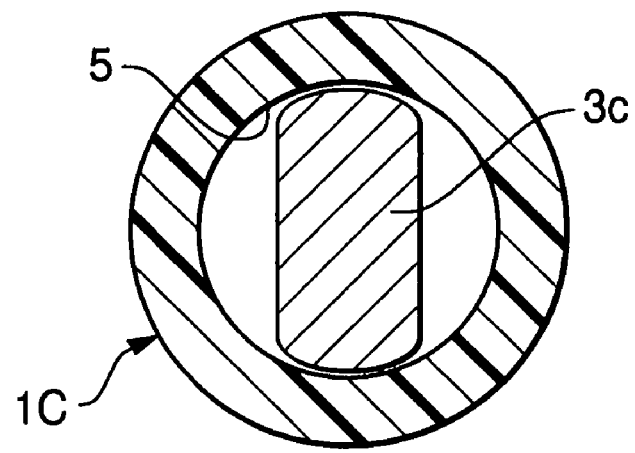
FIGS. 29 and 30 show other examples of a cross-sectional shape of the wide part.
Figure 30:
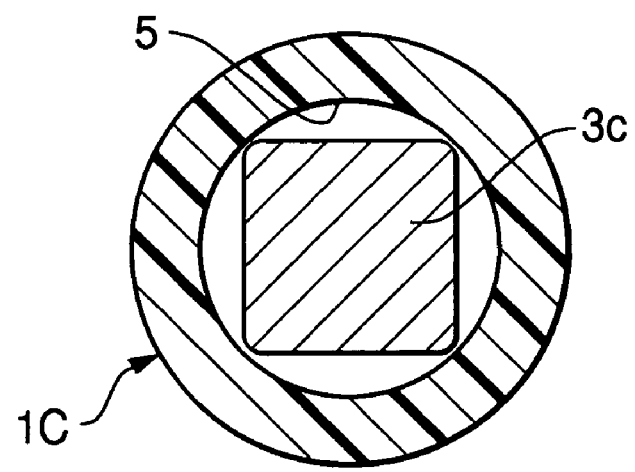

FIGS. 29 and 30 show other examples of a cross-sectional shape of the wide part 3c. The examples of the wide part 3c shown in FIGS. 29 and 30 have an elliptical cross-sectional form and a rectangular cross-sectional form, respectively. The wide part 3c of each of the examples closely fits into an expanded part (e.g. the expanded part 5) of a flexible sheath (e.g. the flexible sheath 1C).

With this structure, an endoscopic treatment using the paddle 3b can be performed in a safe condition while the protruding length of the rod-like part 3a from the tip of the flexible sheath 1D is set at a desired length.

Although the present invention has been described in considerable detail with reference to certain preferred embodiments thereof, other embodiments are possible.

For example, the retractable treatment instrument 20A of the first embodiment may be configured such that the operation wire 2 is roratable about the axis relative to the flexible sheath 1.

The present disclosure relates to the subject matter contained in Japanese Patent Applications No. 2004-085846, filed on Mar. 24, 2004, and No. 2004-101659, filed on Mar. 31, 2004, which are expressly incorporated herein by reference in their entireties.

What is claimed is:

1. A retractable treatment instrument for an endoscope, comprising:
   a flexible sheath comprising at least a tip portion thereof formed of a flexible tube;
   an operation wire inserted in the flexible sheath, the operation wire configured to move in an axial direction within the flexible sheath; and
   a front-end treatment member attached to a tip of the operation wire, a tip portion of the front-end treatment member comprises a flat rod, and a flat shape of the flat rod being oriented along the axial direction of the flexible sheath,
   wherein the front-end treatment member is configured to move back and forth—along the axial direction with respect to a tip of the flexible sheath,
   the front-end treatment member having a wide part elongated in a radial direction of the flexible tube, wherein the wide part is configured to press and broaden the flexible tube from an inside of the flexible tube,
   the wide part being formed integrally with a base portion of the front-end treatment member,
   corner portions of the wide part being cut away such that each edge of the wide part bends at a predetermined degree,
   wherein the flexible sheath has at least one expanded part in which the wide part of the front-end treatment member is configured to fit, the at least one expanded part being located at a part of the flexible sheath comprising the flexible tube, and
   wherein the at least one expanded part is formed by pressing a part of the flexible tube from both sides of the flexible tube so that the part of the flexible tube is expanded in a direction perpendicular to a pressing direction in which the flexible tube is pressed.

2. The retractable treatment instrument according to claim 1, further comprising an operation unit attached to a base of the flexible sheath,
   wherein the operation unit has a movable hook connected to a base of the operation wire, wherein the movable hook is configured to move the operation wire back and forth in the axial direction, and wherein the movable hook comprises a recess provided on an outer circumferential surface of the movable hook.

3. The retractable treatment instrument according to claim 1,
   wherein the operation wire is configured to rotate about a central axis of the operation wire and rotate relative to the flexible sheath.

4. The retractable treatment instrument according to claim 3,
   further comprising a holding ring attached to a base portion of the flexible sheath, wherein the holding ring is configured to rotate the operation wire about the central axis.

5. The retractable treatment instrument according to claim 1,
   wherein an extension of the tip of the operation wire coincides with a center axis of the wide part.

6. The retractable treatment instrument according to claim 1, wherein a pad-like part is provided at a tip portion of the front-end treatment member by elongating the flat shape of the flat rod at the tip portion of the front-end treatment member.

7. The retractable treatment instrument according to claim 1, wherein when the wide part of the front-end treatment member is positioned within the at least one expanded part of the flexible sheath, the front-end treatment member is fully retracted into the flexible sheath.

8. The retractable treatment instrument according to claim 1, wherein:
   the at least one expanded part comprises a plurality of expanded parts; and
   the plurality of expanded parts are arranged along an axial direction of the flexible sheath.

9. The retractable treatment instrument according to claim 8, wherein:
   when the wide part of the front-end treatment member is positioned within a rear end expanded part of the plurality of expanded parts nearest to a base of the flexible sheath, the front-end treatment member is fully retracted into the flexible sheath; and
   when the wide part of the front-end treatment member is positioned within one of the plurality of expanded parts other than the rear end expanded part, the front-end treatment member protrudes from the tip of the flexible sheath by a predetermined length.

10. The retractable treatment instrument according to claim 1,
    wherein the expanded part is formed by expanding the flexible tube uniformly in a radial direction of the flexible tube.

11. The retractable treatment instrument according to claim 1,
    wherein the flexible tube has a cut off part which is formed by cutting off a part of the at least one expanded part projected outward from an outside diameter the flexible tube.

12. The retractable treatment instrument according to claim 1,
    wherein the retractable treatment instrument satisfies a condition:

$$1.07d \leq W \leq 1.26d$$

where W represents a width of the wide part in an elongated direction, and d represents an internal diameter of the flexible sheath.

* * * * *